(12) United States Patent
Lloyd et al.

(10) Patent No.: US 11,304,814 B2
(45) Date of Patent: Apr. 19, 2022

(54) ANTERIOR LOCKING CLIP

(71) Applicant: Biomet UK Healthcare Limited, Bridgend (GB)

(72) Inventors: Russell Lloyd, Swindon Wiltshire (GB); Paul James Kistle, Swindon (GB); Mona Alinejad, London (GB); Robert Metzger, Wakarusa, IN (US)

(73) Assignee: Biomet UK Healthcare Limited, Bridgend (GB)

( * ) Notice: Subject to any disclaimer, the term of this patent is extended or adjusted under 35 U.S.C. 154(b) by 259 days.

(21) Appl. No.: 16/686,898

(22) Filed: Nov. 18, 2019

(65) Prior Publication Data
US 2020/0078182 A1 Mar. 12, 2020

Related U.S. Application Data

(63) Continuation of application No. 15/289,509, filed on Oct. 10, 2016, now Pat. No. 10,517,735.

(30) Foreign Application Priority Data

Oct. 13, 2015 (GB) ..................... 1518074

(51) Int. Cl.
*A61F 2/38* (2006.01)
*A61F 2/30* (2006.01)

(52) U.S. Cl.
CPC ............ *A61F 2/389* (2013.01); *A61F 2/3836* (2013.01); *A61F 2002/30481* (2013.01); *A61F 2220/0008* (2013.01)

(58) Field of Classification Search
CPC ................... A61F 2/389; A61F 2/3836; A61F 2002/30481; A61F 2220/0008
See application file for complete search history.

(56) References Cited

U.S. PATENT DOCUMENTS

| 4,257,129 A | 3/1981 | Volz |
| 4,944,757 A | 7/1990 | Martinez et al. |
| 5,061,271 A | 10/1991 | Van Zile |

(Continued)

FOREIGN PATENT DOCUMENTS

| CN | 202843854 U | 4/2013 |
| CN | 108289741 A | 7/2018 |

(Continued)

OTHER PUBLICATIONS

U.S. Appl. No. 15/289,509, filed Oct. 10, 2016, An Anterior Locking Clip.

(Continued)

*Primary Examiner* — Yashita Sharma
*Assistant Examiner* — Melissa A Hoban
(74) *Attorney, Agent, or Firm* — Schwegman Lundberg & Woessner, P.A.

(57) ABSTRACT

A prosthetic assembly is provided. The prosthetic assembly comprises: a tibial tray having a medial retaining bracket, a lateral retaining bracket and a substantially centrally disposed boss, a medial bearing, a lateral bearing and a retention clip having a pair or arms which engage opposite sides of the boss and trap the medial lateral bearings, against the medial and lateral retaining brackets, respectively. A method of securing bearing components to a prosthetic assembly is also provided.

14 Claims, 6 Drawing Sheets

(56) References Cited

U.S. PATENT DOCUMENTS

| | | | |
|---|---|---|---|
| 5,062,852 A | 11/1991 | Dorr et al. | |
| 5,108,442 A | 4/1992 | Smith | |
| 5,645,604 A | 7/1997 | Schneider et al. | |
| 6,004,352 A | 12/1999 | Buni | |
| 6,126,692 A | 10/2000 | Robie et al. | |
| 8,470,048 B2* | 6/2013 | Wolfson | A61F 2/3868 623/20.33 |
| 8,603,101 B2 | 12/2013 | Claypool et al. | |
| 8,936,648 B2 | 1/2015 | Collard et al. | |
| 9,427,337 B2 | 8/2016 | Claypool et al. | |
| 9,763,807 B2 | 9/2017 | Claypool et al. | |
| 10,517,735 B2 | 12/2019 | Lloyd et al. | |
| 2004/0019384 A1 | 1/2004 | Kirking et al. | |
| 2010/0305709 A1 | 12/2010 | Metzger et al. | |
| 2012/0239159 A1* | 9/2012 | Metzger | A61F 2/3836 623/20.28 |
| 2012/0323333 A1 | 12/2012 | Metzger | |
| 2013/0006375 A1 | 1/2013 | Metzger et al. | |
| 2016/0199171 A1 | 7/2016 | Dodd et al. | |
| 2017/0100254 A1 | 4/2017 | Lloyd et al. | |

FOREIGN PATENT DOCUMENTS

| | | |
|---|---|---|
| EP | 3361992 A1 | 8/2018 |
| FR | 2702651 A1 | 9/1994 |
| GB | 2517154 A | 2/2015 |
| WO | WO-2014043078 A1 | 3/2014 |
| WO | WO-2017066118 A1 | 4/2017 |

OTHER PUBLICATIONS

"U.S. Appl. No. 15/289,509, Advisory Action dated Dec. 28, 2018", 3 pgs.

"U.S. Appl. No. 15/289,509, Final Office Action dated Jun. 13, 2019", 9 pgs.

"U.S. Appl. No. 15/289,509, Final Office Action dated Oct. 18, 2018", 8 pgs.

"U.S. Appl. No. 15/289,509, Non Final Office Action dated Mar. 30, 2018", 13 pgs.

"U.S. Appl. No. 15/289,509, Non Final Office Action dated Apr. 3, 2019", 10 pgs.

"U.S. Appl. No. 15/289,509, Notice of Allowance dated Aug. 30, 2019", 8 pgs.

"U.S. Appl. No. 15/289,509, Response filed Jan. 25, 2018 to Restriction Requirement dated Dec. 14, 2017", 6 pgs.

"U.S. Appl. No. 15/289,509, Response filed May 15, 2019 to Non Final Office Action dated Apr. 3, 2019", 10 pgs.

"U.S. Appl. No. 15/289,509, Response filed Jun. 22, 2018 to Non Final Office Action dated Mar. 30, 2018", 12 pgs.

"U.S. Appl. No. 15/289,509, Response filed Aug. 13, 2019 to Final Office Action dated Jun. 13, 2019", 9 pgs.

"U.S. Appl. No. 15/289,509, Response filed Dec. 17, 2018 to Final Office Action dated Oct. 18, 2018", 10 pgs.

"U.S. Appl. No. 15/289,509, Restriction Requirement dated Dec. 14, 2017", 9 pgs.

"Chinese Application Serial No. 201680058743.1, Office Action dated Mar. 28, 2019", (W/ English Translation), 16 pgs.

"Chinese Application Serial No. 201680058743.1, Response filed Jul. 26, 2019 to Office Action dated Mar. 28, 2019", (W/ English Claims), 9 pgs.

"European Application Serial No. 16784693.0, Response Filed Dec. 18, 2018 to Communication pursuant to Rules 161(2) and 162 EPC dated Jun. 20, 2018", 11 pgs.

"International Application Serial No. PCT/US2016/056248, International Preliminary Report on Patentability dated Apr. 26, 2018", 8 pgs.

"International Application Serial No. PCT/US2016/056248, International Search Report dated Feb. 10, 2017", 6 pgs.

"International Application Serial No. PCT/US2016/056248, Written Opinion dated Feb. 10, 2017", 6 pgs.

"United Kingdom Application Serial No. 1518074.8, Examination Report dated Jul. 26, 2019", 7 pgs.

"United Kingdom Application Serial No. 1518074.8, Office Action dated Oct. 21, 2015", 2 pgs.

"Chinese Application Serial No. 201680058743.1, Office Action dated May 25, 2020", (W/ English Translation), 10 pgs.

"Chinese Application Serial No. 201680058743.1, Office Action dated Nov. 26, 2019", w/ English Translation, 29 pgs.

"Chinese Application Serial No. 201680058743.1, Response filed Jun. 30, 2020 to Office Action dated May 25, 2020", w/ English claims, 11 pgs.

"European Application Serial No. 19199291.6, Extended European Search Report dated Aug. 13, 2020", 6 pgs.

"European Application Serial No. 19199291.6, Response filed May 11, 2021 to Extended European Search Report dated Aug. 13, 2020", 19 pgs.

\* cited by examiner

ANTERIOR LOCKING CLIP

CLAIM OF PRIORITY

This application is a continuation of U.S. patent application Ser. No. 15/289,509, filed on Oct. 10, 2016, which claims priority to United Kingdom Application No. 1518074.8, filed on Oct. 13, 2015, the benefit of priority of each of which is claimed hereby, and each of which is incorporated by reference herein in its entirety.

TECHNICAL FIELD

The present invention relates to a prosthetic assembly comprising at least one bearing held in place on a prosthetic component by a retention clip.

BACKGROUND

Prosthetic tibial components for replacement knee joints typically comprise a tibial tray which is coupled to the tibia of a patient and forms a tibial plateau of the tibia. The tibial component may be a unicondylar tibial component of a partial knee replacement prosthesis which replaces the proximal surface of a medial or a lateral tibial condyle. Alternatively, the tibial component may be part of a total knee replacement prosthesis and may replace substantially the complete proximal surface of the tibia and form a tibial plateau of the medial and lateral tibial condyles.

Often, separate bearing components are coupled to the tibial tray, which may be fixed bearing components or mobile bearing components. Fixed bearing components may additionally comprise mobile portions which are trapped within the fixed bearing. Any fixed bearing components must be coupled to the tibial tray to prevent movement and brackets are often provided on the posterior regions of the tibial tray which couple to the bearing components. The bearing components may comprise a pocketed recess in the posterior region of the bearing to couple with the bracket. The posterior portion of the bearing may be heavily loaded during some knee articulations and if a pocket is provided in this location, reinforcement may be required. In some cases it may be undesirable to provide a pocket in the posterior region of the bearing, for example to improve the rigidity of the posterior portion of the bearing.

During an operation to implant a prosthetic tibial component, which comprises one or more fixed bearing components, the surgeon may select from several bearing components of different thicknesses and may trial fit a bearing component of one thickness before selecting another thickness of bearing component to finally implant. For example, the surgeon may determine that the first bearing selected was too thick and was applying undesirable load into the prosthetic knee joint. The surgeon may trial fit several bearing components before selecting a bearing component with the correct thickness. It is therefore desirable to allow coupling and decoupling of fixed bearing components to be as simple as possible during surgery.

STATEMENTS OF INVENTION

According to a first aspect of the present invention, there is provided a prosthetic assembly comprising: a tibial tray having a medial retaining bracket, a lateral retaining bracket and a substantially centrally disposed boss; a medial bearing; a lateral bearing; and a retention clip having a pair or arms which engage opposite sides of the boss and trap the medial and lateral bearings against the medial and lateral retaining brackets respectively.

The retention clip may trap the medial and lateral bearings by applying a load in the medial and lateral directions to the medial and lateral bearings respectively.

The retention clip may be movably coupled to the prosthetic assembly.

The retention clip may be slidably received within a passage formed in the prosthetic assembly. The passage may be formed between the tibial tray and the medial and/or lateral bearing component. For example, the passage may be formed between the central boss of the tibial tray and the medial and/or lateral bearing component.

The medial and/or lateral bearing component may further comprise a recess provided at a substantially central location of the prosthetic assembly; wherein the passage is formed within the recess.

The passage of the prosthetic assembly may extend in an anterior-posterior direction, and the retention clip may be inserted into the prosthetic assembly in the anterior-posterior direction.

The arm of the retention clip may be displaced by an interference with the centrally disposed boss.

The arms and/or body of the retention clip may be resilient, and the displacement of the arms of the retention clip may cause the retention clip to clamp the central boss.

The deformation of the arms of the retention clip may cause the retention clip to engage the medial and/or lateral bearing components, thereby applying a load to the medial and/or lateral bearing components in the medial and/or lateral direction respectively.

The retention clip may further comprise a relief slot configured to prevent distortion in the body of the clip due to the displacement of the arms.

The tibial tray and/or the medial and/or lateral bearing component may further comprise a clip retaining portion, wherein the retention clip engages the clip retaining portion. Engagement between the retention clip and the clip retaining portion may act to prevent disengagement of the retention clip from the prosthetic assembly.

The clip retaining portion may be provided on the centrally disposed boss of the tibial tray.

The retention clip may comprise an engagement portion configured to engage the clip retaining portion of the tibial tray and/or medial and/or lateral bearing component.

The retention clip may be substantially U-shaped.

The medial and lateral retaining brackets and/or the medial and lateral bearings may be configured such that the bearings are assembled into the prosthetic assembly by translating the medial and lateral bearings in a generally anterior-posterior direction relative to the tibial tray.

The tibial tray may further comprise: a tibial stem comprising a recess; and a resilient element provided within the recess; wherein the resilient element is configured to apply tension to an artificial ligament of the prosthetic assembly; and wherein the resilient element is retained within the recess by the retention clip.

According to a second aspect of the present invention, there is provided a method of securing bearing components to a prosthetic assembly, the method comprising: providing a tibial tray comprising: a medial retaining bracket; a lateral retaining bracket; and a substantially centrally disposed boss; providing a medial bearing component; providing a lateral bearing component; and coupling a retention clip to the prosthetic assembly, the retention clip having a pair or arms which engage opposite sides of the boss and trap the medial and lateral bearings, against the medial and lateral retaining brackets, respectively.

To avoid unnecessary repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

BRIEF DESCRIPTION OF THE DRAWINGS

For a better understanding of the present invention, and to shown more clearly how it may be carried into effect, reference will now be made, by way of example, to the accompanying drawings, in which.

DETAILED DESCRIPTION

Figure 1:
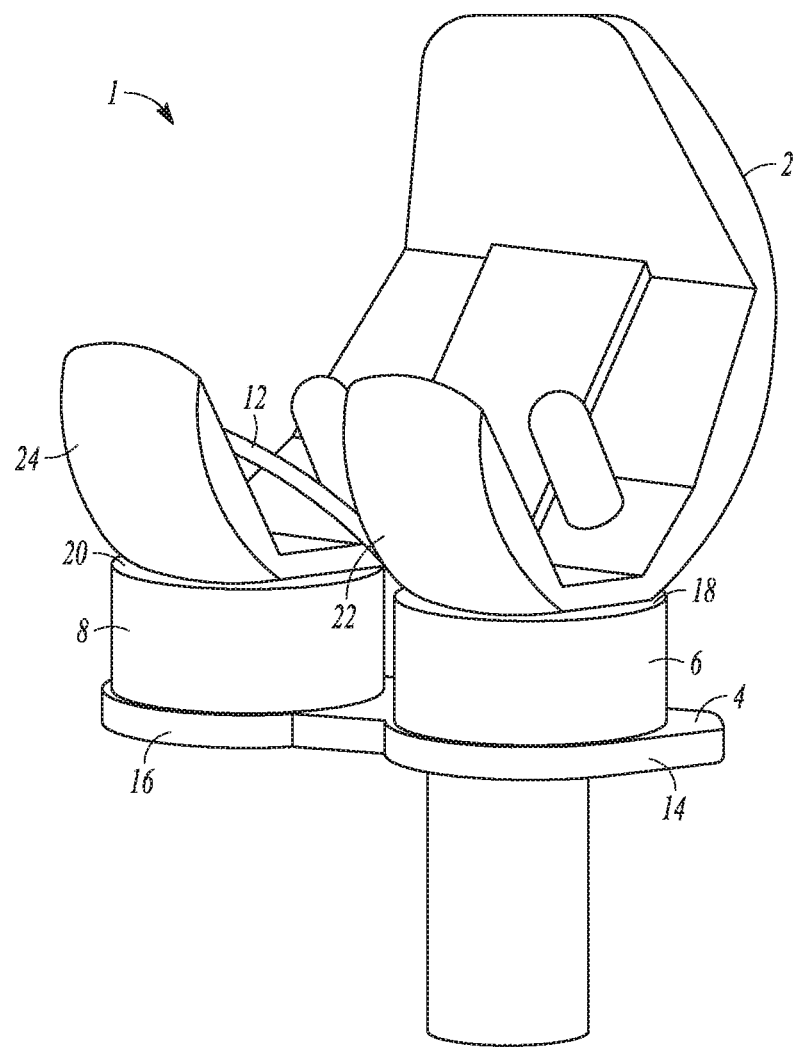
FIG. 1 shows a conventional prosthetic joint assembly.

With reference to FIG. 1, a conventional prosthetic joint assembly 1 comprises a femoral component 2, a tibial component 4, a medial bearing component 6 and a lateral bearing component 8. In use, the femoral component 2 is coupled to a distal end of a femur (not shown) and the tibial component 4 is coupled to a proximal end of a tibia (not shown).

The tibial component 4 comprises a tibial tray with a medial portion 14 and a lateral portion 16. The medial and lateral bearing components 6, 8 are coupled to the medial and lateral portions of the tibial component respectively. The medial and lateral bearing components comprise proximal bearing surfaces 18, 20, which engage cooperating bearing surfaces 22, 24 on the femoral component 2. The bearing surfaces 18, 20, 22, 24 allow the prosthetic joint assembly to articulate and approximate the range of movement of a natural knee joint.

In the prosthetic joint assembly shown in FIG. 1, the medial and lateral bearing components 6, 8 are mobile bearing components, which are movably coupled to the medial and lateral portions 14, 16 of the tibial component. This allows a high flexibility of movement of the joint. The prosthetic assembly 1 may also comprise an artificial ligament 12 which extends between the tibial component 4 and the femoral component 2. The inclusion of the artificial ligament 12 provides stability to the joint and prevents undesirable articulations.

Figure 2:
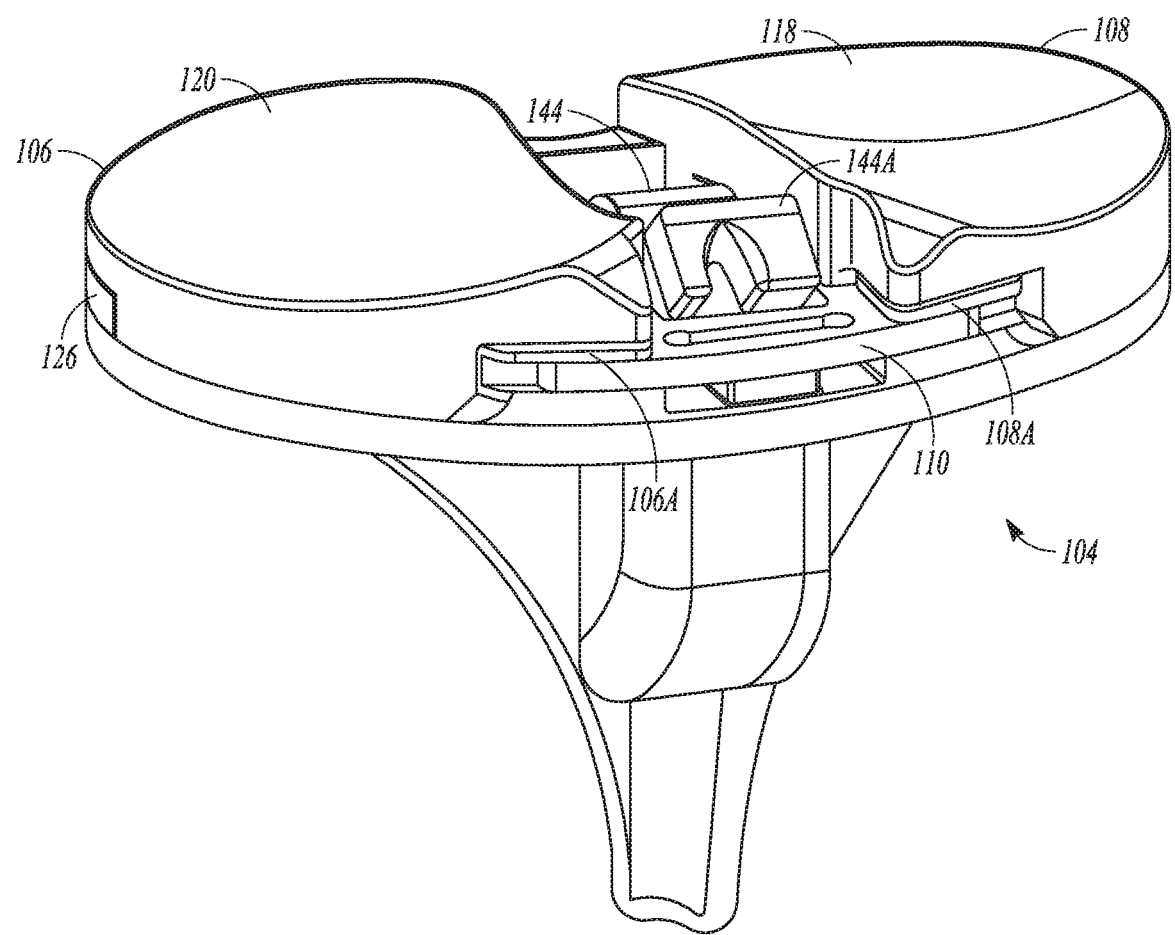
FIG. 2 shows a tibial component of a prosthetic joint assembly, according to an example of the present disclosure.

FIG. 2, shows a tibial component 104 in accordance with an example of the present disclosure. The tibial component 104 comprises a tibial tray, which supports medial and lateral bearing components 106, 108. The medial and lateral bearing components are fixed relative to the tibial component 104. Providing fixed bearing components 106, 108 within the prosthetic assembly 1 improves the stability of the joint.

Figure 3:
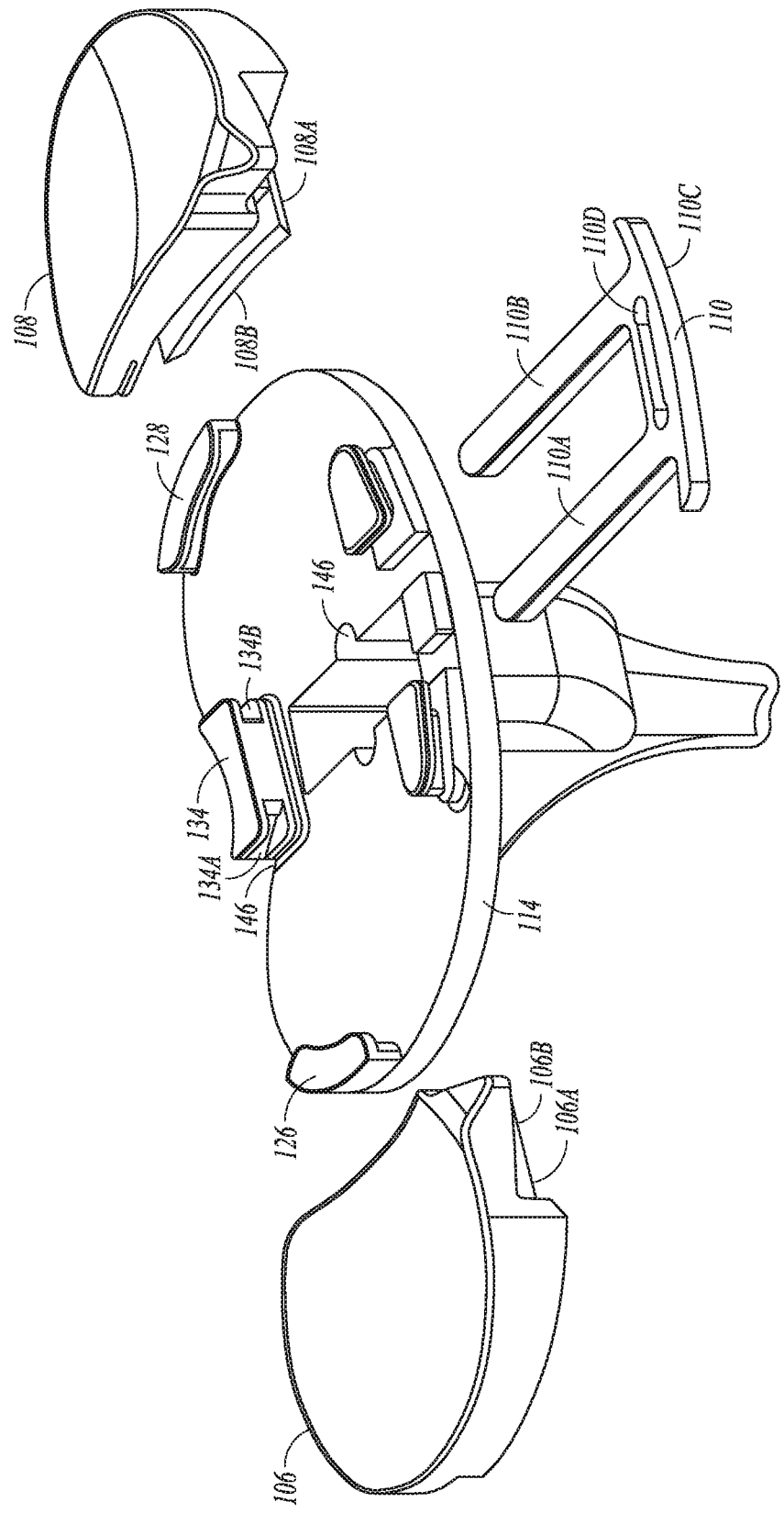
FIG. 3 is an exploded view of a tibial component of a prosthetic joint assembly according to an example of the present disclosure.

Referring to FIGS. 2 and 3, the medial and lateral bearing components 106, 108 comprise recesses 106a, 108a. The recesses 106a, 108a, are formed by slots provided in a medial face of the lateral bearing component 106 and a lateral face of the medial bearing component 108. The slots extend from an anterior face of each bearing component to a posterior face.

As shown in FIGS. 2 and 3, the proximal bearing surfaces 120, 118 of each bearing extend over the recesses 106a, 108a and are supported by a portion of the bearing component provided on a superior side of each slot. The inferior boundary of each slot is formed by distal walls 106b and 108b, which extends laterally from respective bearing components.

Figure 5:
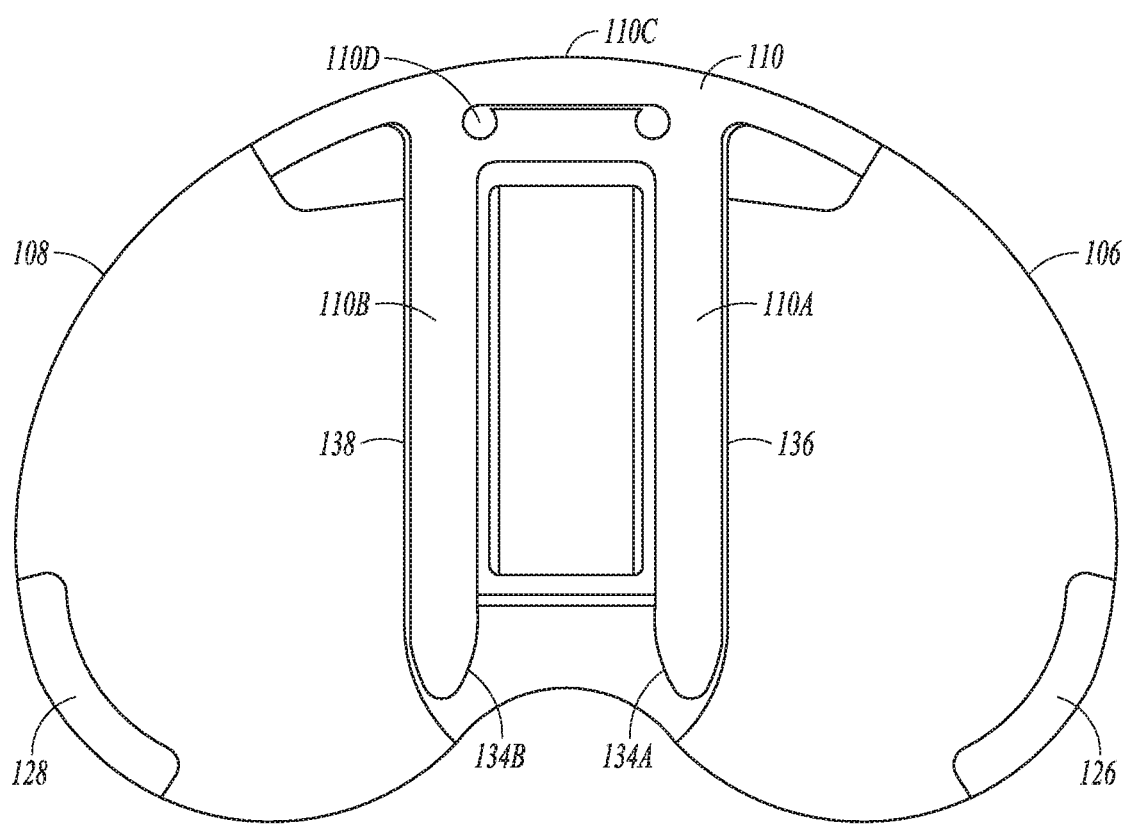
FIG. 5 is a view of a transverse section of a tibial component of a prosthetic assembly according to an example of the present disclosure.

When assembled into the prosthetic assembly 1, the recesses 106a, 108a, define medial and lateral passages 136, 138 of the tibial component 104. The passages 136, 138 are provided at a substantially central location of the tibial component. As shown in FIG. 5, the passages 136, 138 extend from an anterior side of the tibial component 104 towards a posterior side of the tibial component.

The prosthetic assembly 1, as shown in FIGS. 2 to 6, further comprises a retention clip 110. In the example shown, the retention clip 110 is a substantially shaped clip comprising medial and lateral arms 110a, 110b and a body 110c extending between the arms. The retention clip 110 is configured to be received within the medial and lateral passages formed by the recesses 106a, 108a in the medial and lateral bearing components, e.g. the retention clip is configured to be inserted into the tibial component 104 in an anterior-posterior direction. The arms 110a, 110b are tapered at distal ends of the arms to ease alignment with the medial and lateral passages during initial insertion of the retention clip.

When inserted into the medial and lateral passages, the retention clip engages the tibial component 104 and the medial and lateral bearing components 106, 108. The arms of the retention clip are configured to apply loads to the medial and lateral bearing components in the medial and lateral directions respectively, which trap the bearing components against the tibial component 104.

Figure 4:
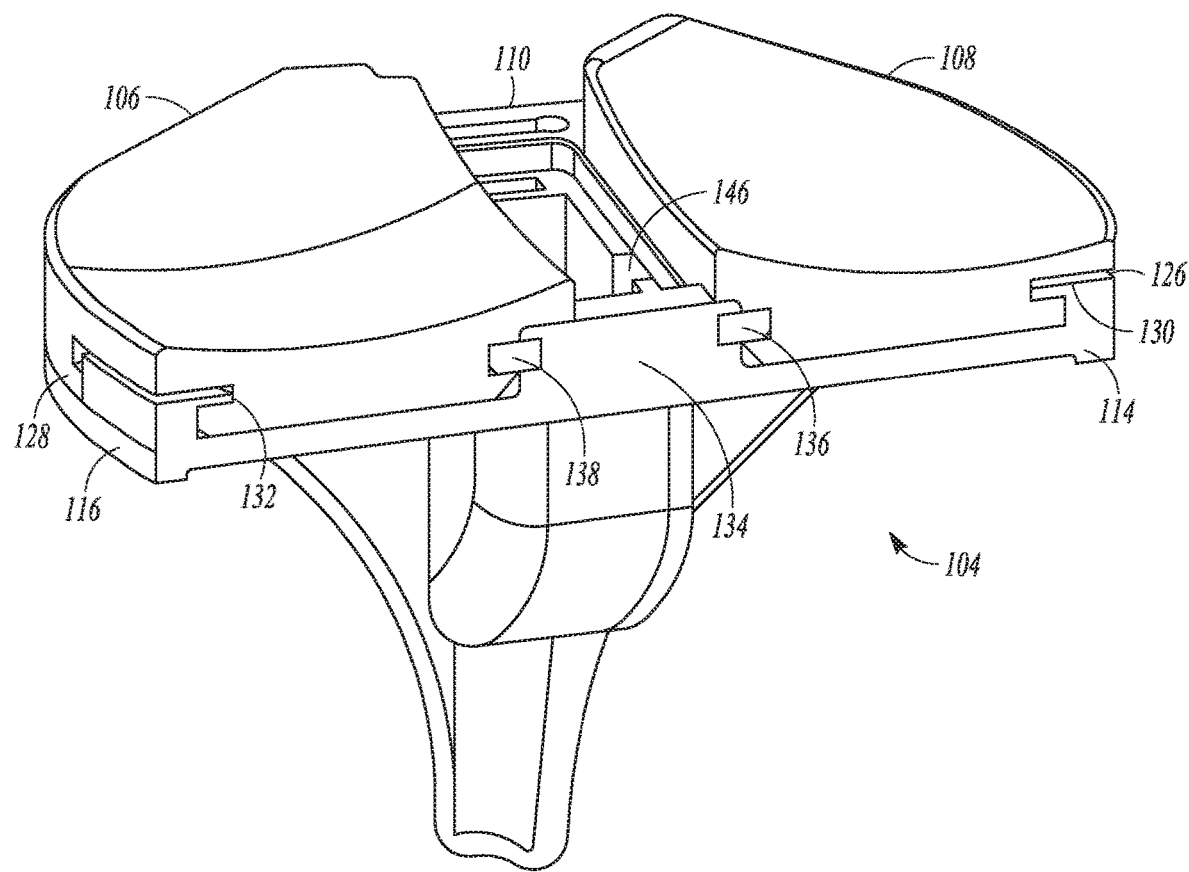
FIG. 4 is a view of a coronal section of a tibial component of a prosthetic joint assembly according to an example of the present disclosure.

With reference to FIGS. 3, 4 & 5, a medial attachment bracket 126 is provided on the medial portion 114 of the tibial tray 104 and a lateral attachment bracket 128 is provided on the lateral portion 116. In the example shown in FIG. 3, the medial attachment bracket 126 is provided on the medial edge of the medial portion 114 and the lateral attachment bracket 128 is provided on the lateral edge of the lateral portion 126. However, it is equally envisaged that the medial and/or lateral attachment bracket 126, 128 may be provided in other locations on the medial and/or lateral portion respectively. For example, the medial and/or lateral attachment bracket may be provided substantially centrally on the medial and/or lateral portion 114, 116 of the tibial tray.

With reference to FIG. 4, the medial and lateral bearing components comprise attachment recesses 130, 132. The medial and lateral bearing components are coupled to the tibial component 4 by translating the medial and lateral bearing components in a generally anterior-posterior direction relative to the tibial tray, such that the attachment recesses 130, 132 engage the medial and lateral attachment brackets 126, 128 respectively.

A boss 134 is provided on the tibial component 104 at a substantially central location on the tibial tray. The boss 134 is provided substantially between the medial and lateral passages 136, 138. The width of the boss is greater than the medio-lateral separation of the passages 136, 138, such that when the retention clip 110 is assembled in the prosthetic assembly 1, the arms of the retention clip 110a, 110b engage either side of the boss 134.

With reference to FIG. 5, the boss 134 comprises medial and lateral interference portions 134a, 134b, which are configured to interfere with the distal ends of the arms 110a, 110b of the retention clip, when the arms are fully received within the passages 136, 138. A relief slot 110d is provided within the retention clip 110 to allow the medial and lateral arms to be displaced medially and laterally respectively, due to their interference with the boss 134, without distorting the body 110c of the clip. The relief slot also reduces the stress at the locations on the retention clip 110 where the arms 110a, 110b join to the body 110c. When the arms 110a, 110b are displaced in this way, strain energy is stored within the arms and body 110a, 110b, 110c of the retention clip causing the arms of the retention clip to apply a clamping load to the boss 134, e.g. the arms and body of the retention clip 110 are resilient. The clamping load provided by the retention clip on the boss acts to resist decoupling of the retention clip 110 from the tibial component 104.

Figure 6:
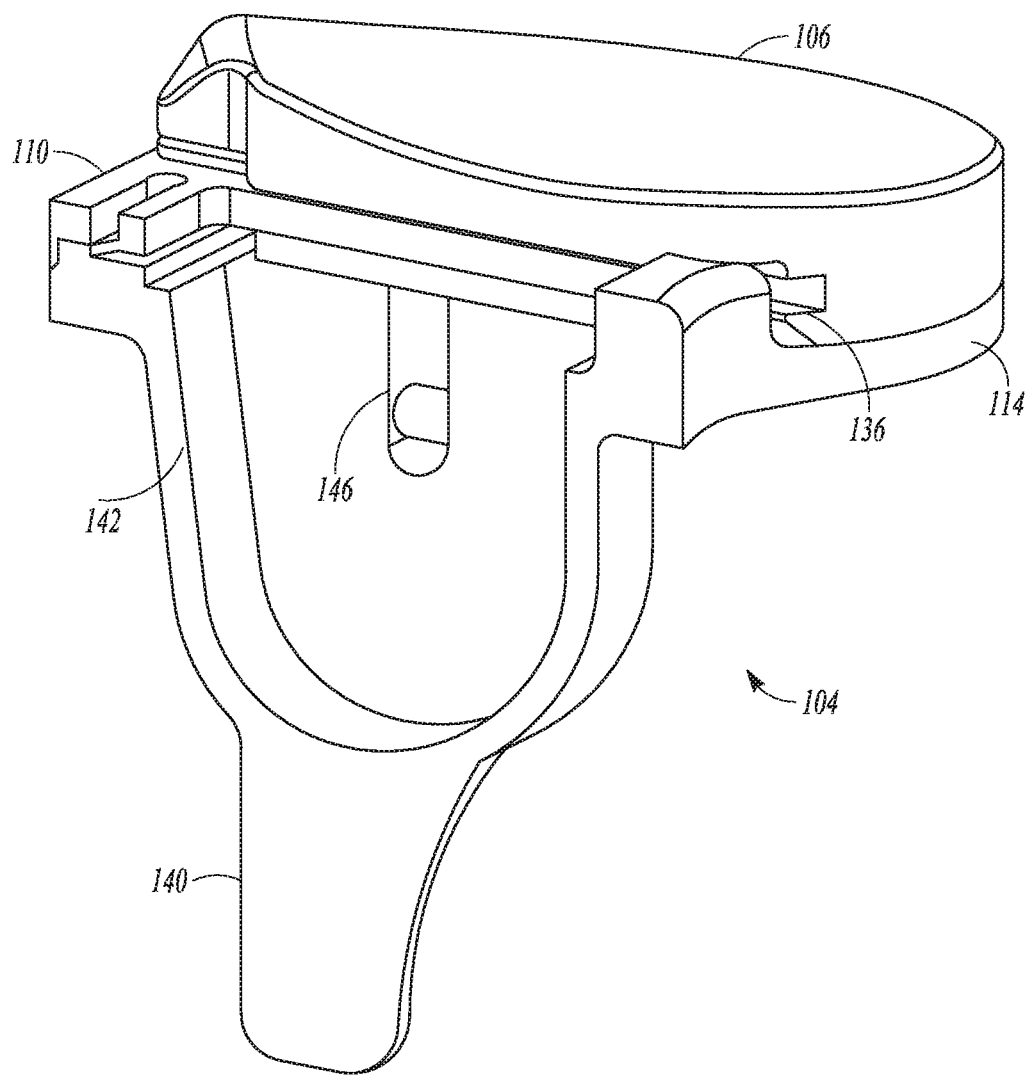
FIG. 6 is a view of a sagittal section of a tibia component of a prosthetic assembly according to an example of the present disclosure.

With reference to FIG. 6, the tibial component 104 comprises a stem 140 having a stem recess 142. The stem recess 142 is configured to receive a resilient element, such as a spiral spring 144, as shown in FIG. 2. In one possible arrangement, the spiral spring comprises a ligament anchor 144a configured to couple to the artificial ligament 12. The spiral spring 144 is configured to apply tension to the ligament 12. The one arrangement the tension in the ligament is adjusted to be substantially equal to the tension in a natural anatomical ligament. The spiral spring 144 comprises one or more projections (not shown) which are received within one or more grooves 146 provided in the stem recess 142. Contact between the grooves 146 and projections allows the spiral spring 144 to extend and contract within the stem recess 142 as load is applied to the ligament 12. As shown in FIGS. 4, 5 and 6, the arms 110a, 110b of the clip 110 cover proximal ends of the grooves 146, and prevent the projections from being removed from the grooves whilst the retention clip is assembled. Consequently, the retention clip can be used to retain the spiral spring 144 within the stem recess 142.

In a method of surgery for implanting the prosthetic assembly 1, the femoral component 2 is implanted onto the distal end of the femur of a patient and the tibial component 104 is implanted onto the proximal end of the tibia of the patient. Bearing components 106, 108, of suitable thicknesses are selected and coupled to the tibial tray by sliding the bearing component in a generally anterior-posterior direction against the tibial component 104, such that the attachment recesses 130, 132, of the medial and lateral bearing components 106, 108 engage the medial and lateral attachment brackets provided on the tibial tray.

Once the medial and lateral bearing components are assembled, the retention clip 110 is coupled to the prosthetic assembly 1 by inserting the medial and lateral arms of the retention clip 110a, 110b into the medial and lateral passages 136, 138 respectively, until the arms of the retention clip engage the boss 134, as described above.

When the retention clip 110 is assembled into the prosthetic assembly 1, the medial and lateral arms of the retention clip 110a, 110b are deflected in the medial and lateral directions respectively, due to their interference with the boss 134. The arms of the retention clip 110 engage the medial and lateral bearing components and apply loads to the bearing components in the medial and lateral directions respectively. The medial and lateral bearing components are thereby trapped against their respective attachment brackets 126, 128.

The distal walls 106b, 108b, which form the inferior boundaries of the recesses 106a, 108a, as described above, prevent the bearing components 106, 108 from being displaced superiorly relative to the tibial component 104 and disengaging from the retention clip 110. This ensures that the bearing components 106, 108 remain coupled to the tibial component 104 during normal use, and are not able to dislocate during articulation of the joint.

Although interference between the arms 110a, 110b of the retention clip 110 and the boss 134, as described above, prevents the retention clip 110 from detaching from the tibial component 104 during normal use, if it is desirable during an operation, a surgeon may remove the retention clip 110 and decouple either or both of the bearing components 106, 108 from the tibial tray 4, for example in order to fit bearing components of a smaller or larger thickness. As the retention clip 110 is installed into the tibial component in an anterior-posterior direction, the retention clip 110 may be removed or installed through a very small incision in the front of a patient's knee, in a minimally invasive surgical procedure.

In another arrangement (not shown), the boss 134 comprises one or more clip retaining portions, such as lugs, provided on the medial and lateral sides of the boss extending in the medal and lateral directions respectively. The retention clip comprises corresponding engagement portions, e.g. recesses, which receive the protrusions. Engagement between the retention clip recesses and the protrusions act to prevent the retention clip from disengaging from the boss.

In another arrangement, the clip 110 may comprise one or more protrusions which are received within one or more corresponding recesses provided on the boss 134. In another arrangement, one or more clip retaining protrusions and/or recesses may be provided on the bearing components 106, 108 and corresponding recesses and/or protrusions may be provided on the retention clip 110, which are configured to engage the clip retaining protrusions and/or recesses provided on the bearing components 106, 108.

It will be appreciated by those skilled in the art that although the invention has been described by way of example, with reference to one or more exemplary examples, it is not limited to the disclosed examples and that alternative examples could be constructed without departing from the scope of the invention as defined by the appended claims.

What is claimed is:

1. A prosthetic assembly comprising:
   a medial beating;
   a lateral bearing;
   a tibial tray comprising:
      a medial retaining bracket positioned at a medial edge of a medial portion of the tibial tray and a lateral retaining bracket positioned at a lateral edge of a lateral portion of the tibial tray;
      a substantially centrally disposed boss;
      a tibial stem comprising a recess; and
      a resilient element configured to be located at least partially within the recess and configured to couple to an artificial ligament of the prosthetic assembly; and a retention clip configured to engage opposite sides of the boss and trap the medial bearing and the lateral bearing against the medial retaining bracket and the lateral retaining bracket, respectively, wherein the retention clip includes a first arm and a second arm each extending anteriorly-to-posteriorly to engage opposite sides of the boss, the first arm configured to engage and trap the medial bearing against the medial retaining bracket and the second arm configured to engage and trap the lateral bearing a, against the lateral retaining bracket.

2. The prosthetic assembly of claim 1, wherein the resilient element is configured to apply tension to the artificial ligament.

3. The prosthetic assembly of claim 2, wherein the retention clip is configured to cover the recess of the tibial stem to retain the resilient element within the recess.

4. The prosthetic assembly of claim 3, wherein the resilient element is configured to contact a groove of the stem recess to allow the resilient element to extend and contract within the stem recess.

5. The prosthetic assembly of claim 4, wherein the resilient element is configured to extend and contract within the stem recess in response to load applied to the artificial ligament.

6. The prosthetic assembly of claim 1, wherein the resilient element is a spiral spring.

7. The prosthetic assembly of claim 1, wherein the retention dip is slidably receivable within a passage formed in the prosthetic assembly.

8. The prosthetic assembly of claim 1, wherein the resilient element is a spiral spring.

9. A prosthetic assembly comprising:
a medial bearing;
a lateral bearing; and
a tibial tray comprising:
   a medial retaining bracket positioned at a medial edge of a medial portion of the tibial tray and a lateral retaining bracket positioned at a lateral edge of a lateral portion of the tibial tray;
   a substantially centrally disposed boss;
   a tibial stem comprising a recess; and
   a resilient element configured to be located at least partially within the recess and configured to couple to an artificial ligament of the prosthetic assembly, wherein the retention clip includes a first arm and a second arm each extending anteriorly-to-posteriorly to engage opposite sides of the boss, the first arm configured to engage and trap the medial bearing against the medial retaining bracket and the second arm configured to engage and trap the lateral bearing against the lateral retaining bracket.

10. The prosthetic assembly of claim 9, wherein the resilient element is configured to apply tension to the artificial ligament.

11. The prosthetic assembly of claim 10, wherein the resilient element is configured to contact one or more grooves of the stem recess to allow the resilient element to extend and contract within the stem recess.

12. The prosthetic assembly of claim 11, wherein the resilient element is configured to extend and contract within the stem recess in response to forces applied to the artificial ligament.

13. The prosthetic assembly of claim 9, further comprising:
a retention clip configured to engage opposite sides of the boss and trap the medial bearing and the lateral bearing against the medial retaining bracket and the lateral retaining bracket, respectively.

14. The prosthetic assembly of claim 9, wherein at least one of the medial bearing and the lateral bearing is configured for assembly into the prosthetic assembly by translating the bearing in a generally anterior-posterior direction relative to the tibial tray.

* * * * *

UNITED STATES PATENT AND TRADEMARK OFFICE
CERTIFICATE OF CORRECTION

| | |
|---|---|
| PATENT NO. | : 11,304,814 B2 |
| APPLICATION NO. | : 16/686898 |
| DATED | : April 19, 2022 |
| INVENTOR(S) | : Lloyd et al. |

It is certified that error appears in the above-identified patent and that said Letters Patent is hereby corrected as shown below:

In the Claims

In Column 6, Line 55, in Claim 1, delete "beating;" and insert --bearing;-- therefor In Column 7, Line 10, in Claim 1, after "bearing", delete "a,"

In Column 7, Line 28, in Claim 7, delete "dip" and insert --clip-- therefor

Signed and Sealed this
Seventh Day of June, 2022

Katherine Kelly Vidal
*Director of the United States Patent and Trademark Office*